United States Patent [19]

Ungarelli et al.

[11] Patent Number: 4,853,488

[45] Date of Patent: Aug. 1, 1989

[54] PROCESS FOR THE PREPARATION OF (2,2)-PARACYCLOPHANE AND DERIVATIVES THEREOF

[75] Inventors: Raffaele Ungarelli, Trecate; Loris Sogli, Novara, both of Italy

[73] Assignee: Montedison S.p.A., Milan, Italy

[21] Appl. No.: 179,250

[22] Filed: Apr. 8, 1988

[30] Foreign Application Priority Data

Apr. 10, 1987 [IT] Italy .................................. 20059 A/87

[51] Int. Cl.$^4$ ........................ C07C 21/24; C07C 25/18
[52] U.S. Cl. .................................................... 570/184
[58] Field of Search ................................ 570/184, 185

[56] References Cited

U.S. PATENT DOCUMENTS 4,783,561 11/1988 Pregaglia et al. ................... 570/184
4,795,838 1/1989 Bornengo et al. .................. 570/184

OTHER PUBLICATIONS

"Organic Syntheses, Collective vol. 5", John Wiley & Sons, Inc., New York, London–Sydney–Toronto, (1973), pp. 883–886.

Primary Examiner—Werren B. Lone
Attorney, Agent, or Firm—Stevens, Davis, Miller & Mosher

[57] ABSTRACT

Process for the preparation of (2,2)-paracyclophane or derivatives thereof by the Hofmann elimination of p-methylbenzyl-trimethylammonium hydroxide or derivatives thereof, in an aqueous solution of an alkali metal hydroxide, wherein said elimination is carried out in the presence of a compound of the formula (I):

$$(R)_m\text{---}A\text{---}(X)_n \qquad (I)$$

wherein A represents an aromatic group, X an electron donor group, R hydrogen or an alkyl group containing from 1 to 4 carbon atoms, n is an integer from 1 to 6, and m is zero or an integer from 1 up to a value such that the sum m+n is equal to the number of substitutable positions in the aromatic group.

7 Claims, No Drawings

PROCESS FOR THE PREPARATION OF (2,2)-PARACYCLOPHANE AND DERIVATIVES THEREOF

DESCRIPTION OF THE INVENTION

The present invention relates to a process for the preparation of (2,2)-paracyclophane and derivatives thereof having the formula:

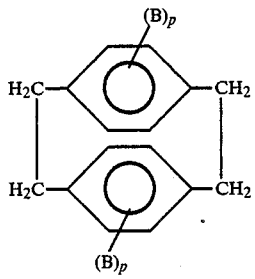

wherein B may be a halogen, an alkyl, an aralkyl, or a halogenaralkyl radical having from 1 to 20 carbon atoms, and b is zero or an integer from 1 to 4.

More particularly, the present invention relates to a process for preparing (2,2)-paracyclophane and its derivatives having the formula (II), starting from a p-methylbenzyltrimethylammonium derivative having the formula:

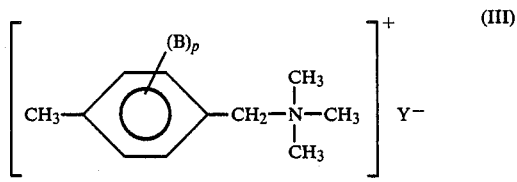

wherein B and p are the same as defined above, and y is a hydroxy radical or a halogen, by the Hofmann elimination.

(2,2)-paracyclophane and its derivatives such as dichloro-(2,2)-paracyclophane, tetrachloro-(2,2)-paracyclophane, tetramethyl-(2,2)-paracyclophane, dimethyl-dichloro-(2,2)-paracyclophane, diethyl-(2,2)-paracyclophane, dibromo-(2,2)-paracyclophane, etc., are products well known in the literature and are generally utilized as intermediates in the preparation of the corresponding poly-p.xylylenes. Said polymers, and in particular poly-p.xylylene and its chlorinated derivatives, are advantageously utilized in the form of coating films in the field of conformal coating, obtained by application according to the vacuum vapor deposition technique, in the field of electronics.

Various processes have been proposed for preparing (2,2-paracyclophane and its derivatives (II). However, such known processes are not fully satisfactory and are not suitable for being adopted on an industrial scale, mainly due to the low productivity of the process and to the difficulty in recovering the product from the reaction mixture.

Thus, for example, Organic Syntheses, Collective Vol. 5, John Wiley & Sons, Inc., New York-London-Sydney-Toronto, 1973, pages 883–886, describes a process for preparing (2,2)-paracyclophane by the Hofmann elimination starting from p-methylbenzyltrimethylammonium hydroxide obtained by reacting the corresponding bromide with silver oxide.

The elimination is carried out in the presence of an alkaline medium and an inert organic solvent (e.g., toluene) and a yield of about 10% is attained.

According to European patent application No. 108,297, it is possible to increase the reaction yield by carrying out the Hofmann elimination in an alkaline medium and in the presence of large amounts of dimethylsulphoxide. The large volumes and the long reaction times, generally exceeding 50 hours, lead to a low productivity in spite of high yields (about 70%). Furthermore, the recovery of dimethylsulphoxide and the unsatisfactory quality of the resulting product render this process little attractive for industrial scale utilization.

Generally, in all the known processes for producing (2,2)-paracyclophane, rather large amounts of poly p.xylylene are formed, which, in the presence of large amounts of organic solvent in the reaction medium, assumes a gelatine-like appearance and is difficult to be filtered off.

According to the present invention, it has now been discovered that (2,2)-paracyclophane and derivatives thereof having formula (II) may be prepared in a pure form, with high industrial yields, even higher than 80% by mols, by carrying out the Hofmann elimination of p-methylbenzyltrimethylammonium hydroxide, optionally substituted in the nucleus, of formula (III) in an alkaline aqueous solution and in the presence of at least a catalytic amount of a compound having the formula (I):

wherein A represents an aromatic group, X an electron donor group, R hydrogen or an alkyl radical having from 1 to 4 carbon atoms, n is an integer from 1 to 6, and m is zero or an integer from 1 up to a value such that the sum m+n is equal to the number of substituable positions in the aromatic group A.

The term electron donor group means all radicals containing a covalent bond wherein both electrons of the doublet are provided by the same atom.

Examples of electron donor groups are:
the methyl group;
—$OR_1$ radicals wherein $R_1$ is hydrogen, an alkyl radical having from 1 to 6 carbon atoms or an aryl, alkylaryl or aryl-alkyl radical having from 6 to 18 carbon atoms;
—$N(R_1)_2$ radicals wherein $R_1$ has the same above-reported meaning.

According to the present invention, the compounds of formula (I) wherein A represents a phenyl or naphthyl group, n is equal to 2 or 3, m is zero or an integer from 1 to 3, and X has the above-reported meanings, which may be equal or different from each other, are particularly preferred.

A non-limitative list of compounds having formula (I) is: 1,4-hydroquinone; ortho-, meta- and para-aminophenol; ortho-, meta- and para-phenylene-diamine; 2,6-di-tert.-butylparacresol; p.p'-diamine-diphenylmethane; phenol; N,N'-di-phenyl-1,4-phenylene-diamine; 3-tert.butyl-4-hydroxy-anisole; 2,4-ditert.butyl-phenol; hydroquinone mono-ethyl ether, etc.

These compounds are well known in the literature or can be found on the market or may be prepared according to conventional methods of synthesis.

The catalytic compound of formula (I) may be used in amounts which also may vary over a wide range, depending on the values taken by the other parameters, such as the temperature, reaction times, etc. However, excellent results are achieved by using molar amounts between 5 and about 30%, preferably between 10 and 20%, referred to the p-methylbenzyltrimethylammonium derivative optionally substituted in the nucleus, of formula (III).

According to this invention, the Hofmann elimination is carried out in an aqueous solution and preferably in the absence of a solvent.

The aqueous phase is constituted by an alkali metal hydroxide solution having a concentraion higher than 10% by weight. As an alkali metal hydroxide, sodium or potassium hydroxide may be used. The concentration of the aqueous solution is preferably maintained during the Hofmann elimination reaction at a concentration between about 20 and 50% by weight.

In the process of the present invention, the Hofmann elimination is carried out on p.methylbenzyltrimethylammonium hydroxide which may be either prepared separately or formed in situ by the reaction of the corresponding halide with the alkali metal hydroxide.

The Hofmann elimination is carried out at a temperature between 50° and 150° C., and preferably between 90° and 130° C., and for a time between 1 and 50 hours, and, preferably for 2 to 10 hours.

Even if not necessary, inert organic solvents which are immiscible with water, such as, e.g., toluene, xylene, benzene, or tetraline, may be added to the reaction medium.

At the end of the elimination reaction, the resulting product is separated according to per se known and substantially conventional methods.

The process of this invention permits one to obtain, with industrially acceptable yields, (2,2)-paracyclophane and its derivatives substituted in the nucleus, with a high degree of purity (above 99.5%) and a high productivity.

The present invention is still further elucidated by the following examples, which however are to be construed as merely illustrative and not limitative of the invention. In the examples, unless otherwise specified all parts, percentages, and ratios are by weight.

EXAMPLE 1 (COMPARATIVE TEST)

Into a 1,000 ml flask equipped wit a stirrer, thermometer, and condenser, there were charged:
100 g of an aqueous solution containing 40% by weight of NaOH (1 mole); and
62.5 g of an aqueous solution containing 63.9% by weight of p-methylbenzyltrimethylammonium chloride (0.2 moles).

Under continuous stirring, the solution was gradually heated to a temperature of 120° C. The NaOH concentration was maintained at 35% by weight. The solution was maintained at the boiling temperature over the course of 6 hours.

The resulting (2,2)-paracyclophane was separated from the reaction mass by solubilization in 300 ml of xylene. For this purpose, xylene was added to the reaction mass and the slurry was maintained at full reflux under stirring during 0.5 hour. The reaction mass was filtered at 95° C., the aqueous phase was separated from the organic solution, and this solution was repeatedly washed with water and concentrated to a small volume. The xylene solution was cooled down to 20° C. and the precipitated solid was recovered by filtration. After washing the solid with acetone and drying, there were obtained 1.08 g of a crystalline white solid (yield 5.2% by moles), having a melting point of 283°–285° C., which, on gas-chromatographic analysis, proved to be (2,2)-paracyclophane having a degree of purity of about 99.5%.

EXAMPLES 2–12

Example 1 is repeated by adding a compound, of the type and in an amount reported in the following Table 1, to the NaOH aqueous solution.

The amount of the obtained (2,2)-paracyclophane, the relevant melting point, and the reaction yield are reported in the following Table 1.

TABLE 1

| Example No. | Added Compound Type | Amount by moles | Obtained Product Amount g. | Obtained Product Amount moles | Yield % by moles | Melting Point °C. |
|---|---|---|---|---|---|---|
| 2 | Hydroquinone | 0.016 | 5.1 | 0.0245 | 24.5 | 282–286 |
| 3 | Ortho aminophenol | 0.016 | 5.1 | 0.0245 | 24.5 | 282–287 |
| 4 | Meta aminophenol | 0.016 | 4.8 | 0.0230 | 23 | 282–284 |
| 5 | Para aminophenol | 0.016 | 9.1 | 0.0438 | 43.8 | 283–285 |
| 6 | Para aminophenol | 0.033 | 8.4 | 0.0404 | 40.4 | 281–284 |
| 7 | Ortho phenylendiamine | 0.016 | 6.3 | 0.0303 | 30.3 | 282–284 |
| 8 | Meta phenylenediamine | 0.016 | 4.7 | 0.0226 | 22.6 | 282–286 |
| 9 | Para phenylenediamine | 0.008 | 7.3 | 0.0351 | 35.1 | 283–285 |
| 10 | Para phenylenediamine | 0.016 | 10.5 | 0.0505 | 50.5 | 283–284 |
| 11 | Para phenylenediamine | 0.024 | 11.1 | 0.0533 | 53.3 | 282–285 |
| 12 | p.p'di-amino-diphenyl methane | 0.016 | 5.9 | 0.0284 | 28.4 | 283–287 |

What is claimed is:

1. A process for preparing (2,2)-paracyclophane and derivatives thereof of the formula:

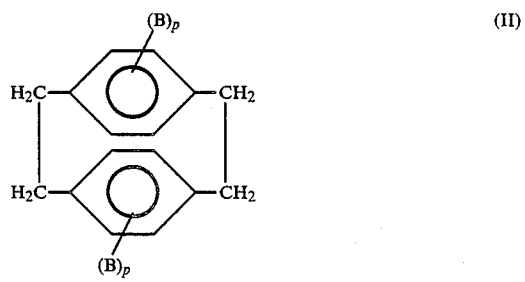

wherein B is a halogen atom, an alkyl radical, an aralkyl radical, or a halo-aralkyl radical, having up to 20 carbon atoms, and p is zero or an integer from 1 to 4, by the Hofmann elimination of a p-methylbenzyltrimethylammonium derivative of the formula:

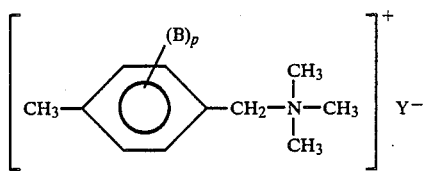

wherein B and p are the same as defined hereinabove, and Y is a hydroxy radical or a halogen atom, in an alkaline aqueous solution, characterized in that said elimination is carried out at a temperature of 50° to 150° C. and in the presence of at least a catalytic amount of a compound having the formula:

$$(R)_m-A-(X)_n \qquad (I)$$

wherein A is an aromatic group, X is an electron donor group, R is a hydrogen atom or an alkyl radical having from 1 to 4 carbon atoms, n is an integer from 1 to 6, and m is zero or an integer from 1 up to a value such that the sum m+n is equal to the number of substitutable positions in the aromatic group A, and wherein the electron-donor group X is selected from the group consisting of $-OR_1$, $-N(R_1)_2$ and $-SR_1$, and wherein $R_1$ is hydrogen, an alkyl radical having from 1 to 6 carbon atoms, an aryl radical, an alkyl-aryl radical, or an arylalkyl radical containing from 6 to 18 carbon atoms.

2. The process according to claim 1, wherein in the compound of formula (I) A represents a phenyl or naphthyl group, n is equal to 2 or 3, m is zero or an integer from 1 to 3, and X has the values reported in claim 1, which may be equal or different from each other.

3. The process according to claim 1, characterized in that the compound of formula (I) is selected from the group consisting of: 1,4-hydroquinone; ortho-, meta- and paraaminophenol; ortho-, meta- and para-phenylene-diamine; 2,6-ditert.butyl-para-cresol; p.p.'-diamino-di-phenylmethane; phenol; N,N'-di-phenyl-1,4-phenylene diamine; 3-tert.butyl-4-hydroxy-anisole; 2,4-di-tert.butyl-phenol; and hydroquinone-monomethyl ether.

4. The process according to claim 1, characterized in that the catalyst of formula (I) is used in a molar amount ranging from 5 to 30% based on the p-methylbenzyltrimethylammonium derivative of formula (III), and preferably from 10 to 20%.

5. The process according to claim 1, characterized in that the concentration of the aqueous solution of alkali metal hydroxide is higher than 10% by weight and is maintained, during the Hofmann elimination reaciton, at from 20 to 50% by weight.

6. The process according to claim 1, characterized in that the p.methylbenzyltrimethylammonium hydroxide of formula (III) is prepared in situ by the reaction of the corresponding halide with the alkali metal hydroxide present in the reaction medium.

7. The process according to claim 1, characterized in that the Hofmann elimination is carried out at a temperature between 90° and 130° C., over the course of 1 to 50 hours, preferably 2 to 10 hours, and preferably in the absence of a solvent.

* * * * *